United States Patent
Appleby

(10) Patent No.: US 10,548,528 B2
(45) Date of Patent: Feb. 4, 2020

(54) SMARTPHONE DEVICE FOR BODY ANALYSIS

(71) Applicant: Ryan James Appleby, Minneapolis, MN (US)

(72) Inventor: Ryan James Appleby, Minneapolis, MN (US)

( * ) Notice: Subject to any disclaimer, the term of this patent is extended or adjusted under 35 U.S.C. 154(b) by 1166 days.

(21) Appl. No.: 14/820,554

(22) Filed: Aug. 7, 2015

(65) Prior Publication Data

US 2017/0035352 A1 Feb. 9, 2017

(51) Int. Cl.
*A61B 5/00* (2006.01)
*A61B 8/00* (2006.01)

(52) U.S. Cl.
CPC .......... *A61B 5/4872* (2013.01); *A61B 5/0064* (2013.01); *A61B 5/6843* (2013.01); *A61B 5/6898* (2013.01); *A61B 5/7275* (2013.01); *A61B 8/461* (2013.01); *A61B 8/56* (2013.01); *A61B 5/002* (2013.01)

(58) Field of Classification Search
CPC ..... A61B 5/002; A61B 5/0064; A61B 5/1075; A61B 5/4872; A61B 5/6843; A61B 5/6898; A61B 5/7275; A61B 8/4227; A61B 8/4427; A61B 8/461; A61B 8/5523; A61B 8/56; G16H 50/30
USPC ........................................................ 600/437
See application file for complete search history.

(56) References Cited

U.S. PATENT DOCUMENTS

| | | | | |
|---|---|---|---|---|
| 2002/0095087 A1* | 7/2002 | Mourad | ............... | A61B 5/0048 600/442 |
| 2002/0123695 A1* | 9/2002 | Kawanishi | ........... | A61B 5/0537 600/547 |
| 2003/0158501 A1* | 8/2003 | Uchida | ................ | A61B 5/0059 600/587 |
| 2003/0208113 A1* | 11/2003 | Mault | ................ | A61B 5/14532 600/316 |
| 2003/0236466 A1* | 12/2003 | Tarjan | .................. | A61B 5/0408 600/508 |
| 2004/0077969 A1* | 4/2004 | Onda | .................... | A61B 5/0537 600/547 |
| 2005/0107717 A1* | 5/2005 | Yamamoto | ........... | A61B 5/0537 600/547 |
| 2005/0197575 A1* | 9/2005 | Kondoh | ............... | A61B 5/1075 600/438 |

(Continued)

FOREIGN PATENT DOCUMENTS

| | | | | |
|---|---|---|---|---|
| CN | 104958075 A | * | 10/2015 | ........... A61B 5/1455 |
| CN | 104958075 A | * | 10/2015 | ........... A61B 5/1455 |

(Continued)

*Primary Examiner* — Carl H Layno
*Assistant Examiner* — Michael J Lau
(74) *Attorney, Agent, or Firm* — Patterson Thuente Pedersen, PA

(57) ABSTRACT

A device designed to empower users to take control of their health by becoming aware of how their physical and mental health is affected by their lifestyle choices. In embodiments, the device can comprise a housing, at least one emitter source disposed within the housing, a first sensing element configured to detect a reflected portion of the at least one energy beam and generate a first signal corresponding to a measured composition of subcutaneous fat tissue, and a second sensing element configured to detect a plurality of physiological parameters.

18 Claims, 16 Drawing Sheets

(56) References Cited

U.S. PATENT DOCUMENTS

| | | | | |
|---|---|---|---|---|
| 2005/0222516 | A1* | 10/2005 | Kasahara | A61B 5/0537 600/547 |
| 2006/0085049 | A1* | 4/2006 | Cory | A61B 5/0536 607/48 |
| 2007/0038092 | A1* | 2/2007 | Jean-Claude | A61B 5/4872 600/438 |
| 2008/0221519 | A1* | 9/2008 | Schwach | A61B 5/0059 604/116 |
| 2009/0274341 | A1* | 11/2009 | Wilson | G01N 33/12 382/110 |
| 2010/0158332 | A1* | 6/2010 | Rico | A61B 5/4312 382/128 |
| 2010/0191088 | A1* | 7/2010 | Anderson | A61B 17/7074 600/373 |
| 2011/0257496 | A1* | 10/2011 | Terashima | G06F 19/00 600/347 |
| 2011/0295144 | A1* | 12/2011 | Murakawa | A61B 5/0537 600/547 |
| 2012/0016210 | A1* | 1/2012 | Kim | A61B 5/02416 600/301 |
| 2012/0259311 | A1* | 10/2012 | Hirshberg | A61M 37/0015 604/506 |
| 2013/0041343 | A1* | 2/2013 | Toumazou | G06F 19/3468 604/504 |
| 2013/0301060 | A1* | 11/2013 | Murakawa | A61B 5/0537 356/634 |
| 2014/0121522 | A1* | 5/2014 | Kiyose | A61B 8/4494 600/449 |
| 2014/0121564 | A1* | 5/2014 | Raskin | A61B 5/0022 600/587 |
| 2014/0142864 | A1* | 5/2014 | Spears | A61B 5/1112 702/19 |
| 2014/0143064 | A1* | 5/2014 | Tran | A61B 5/0022 705/14.66 |
| 2014/0247151 | A1* | 9/2014 | Proud | A61B 5/0024 340/870.02 |
| 2014/0296748 | A1* | 10/2014 | Itagaki | A61B 5/4872 600/587 |
| 2015/0099943 | A1* | 4/2015 | Russell | A61B 5/0059 600/301 |
| 2015/0119717 | A1* | 4/2015 | Yoshida | A61B 8/4411 600/447 |
| 2016/0008634 | A1* | 1/2016 | Payne | A61B 8/4227 600/411 |
| 2016/0143558 | A1* | 5/2016 | Chernokalov | A61B 5/0507 600/430 |
| 2016/0192867 | A1* | 7/2016 | Esenaliev | A61B 5/0095 600/316 |
| 2016/0249857 | A1* | 9/2016 | Choi | A61B 5/0537 600/547 |
| 2017/0049390 | A1* | 2/2017 | Zhang | A61B 5/4872 |
| 2018/0199882 | A1* | 7/2018 | Klee | A61B 5/4818 |

FOREIGN PATENT DOCUMENTS

| | | | | |
|---|---|---|---|---|
| WO | WO 2015063360 A1 | * | 5/2015 | A61B 5/053 |
| WO | WO-2015063360 A1 | * | 5/2015 | A61B 5/053 |
| WO | WO 2015102156 A1 | * | 7/2015 | A61B 5/6898 |
| WO | WO-2015102156 A1 | * | 7/2015 | A61B 5/6898 |

* cited by examiner

ND DEVICE FOR BODY
SMARTPHONE DEVICE FOR BODY ANALYSIS

RELATED APPLICATIONS

This application claims the benefit of priority to U.S. Provisional Application Ser. No. 62/031,438, filed on Jul. 31, 2014, which is hereby incorporated by reference herein in its entirety.

FIELD OF THE INVENTION

This invention relates generally to systems and methods for assessing body composition, and more particularly to a portable subcutaneous fat diagnostic device for use with a mobile device.

BACKGROUND OF THE INVENTION

Humans have always been in the pursuit of health and happiness. The most sought after goal in the health and fitness industry by consumers is to lose subcutaneous adipose tissue (SCAT) (hereinafter also referred to as "SCAT", "fat", "body fat", "storage site", "[body] fat storage site") specifically in target areas such as the abdomen/mid-section and hips/thighs. In peoples' quest to lose this fat, they commonly use various tools, instruments, devices, and products to analyze their body fat to see if any lifestyle changes are working to eliminate said fat. With the currently available products on the market, there lacks a device that is easy to use, and is accurate, specific, and has consistency in repeatability in order to deliver the most effective measurements, which can be correlated and analyzed further to determine even further relationships and correlations, to make even more effective decisions towards positively impacting their health.

The most common technology used in consumer-driven devices on the market to measure body fat is Bio-electrical Impedance Analysis (BIA). In BIA systems, a two-electrode configuration is generally used to detect changes in a person's body composition mass.

Although such technology excels at ease-of-use for the consumer, it lacks accuracy and specificity in determining body fat. Another conventional approach includes the use of the "skin-fold" method which measures the thickness of skin and fat at certain sites on the body with a caliper-like device, which is the most specific pertaining to location on the body. Drawbacks to such techniques include a lack of accuracy, repeatability, and ease of use for users.

For example, even when data pertaining to a person's bodily fat is gathered, the information is not readily available such that it provides a user with the ability to accurately interpret the data, thereby enabling the user to make better lifestyle changes and decisions as it relates to their health and fitness goals including decreasing SCAT. When an apparatus that measures overall body fat or overall body fat percentages is utilized to determine the effectiveness of a particular variable, it doesn't give as accurate, credible, or relevant information due to its lack of specificity. For example, if a person were to gain 2 oz of fat in their legs and lose 2 oz of fat in their abdominal area—there would be no overall net change in body fat amount/percentage, although there was a change that occurred.

Additionally, there is evidence to support that the changes in amounts of body fat stored relative to specific locations in the body are be influenced by hormonal changes within the body (refer, e.g., to references 1-25 discussed with reference to FIG. 11). Hormones are the communication medium between organs in the body, and are ultimately the reasons/determining factor in why the human body stores fat and where it will store the fat. Decreasing body fat in a healthy manner for the long-term is only possible if the hormones are in balance. Hormonal imbalances display themselves in multiple ways that can be assessed and measured—so by looking for the related ways the hormonal imbalances show themselves that can be assessed and measured conveniently and non-invasively, we can gain insight into what is going on non-invasively. Such measurements, for example, can be correlated and analyzed further to determine relationships and correlations, which allows a user to make more effective health related decisions that positively impact their health. If we are able to understand what is going on hormonally, we can move one step closer in the process to understanding the true catalyst and its ultimate response on the entire body—allowing the system to address (not overlook) the root-causes of unwanted health variables, and not focusing on addressing the symptoms, which is futile.

Anytime a decision is made to affect the health of a person, it is merely an educated guess. Everything is simply a means of trial and error when trying to create change(s) with our health. For example, the most highly educated experts in the industry (doctors) are merely guessing when they give a client a prescription—they are never 100% certain of what the effects of a certain drug will be with every patient. So if the experts concerning the workings of the human body are making educated guesses when making suggestions on improving health; it is currently the best means we have/industry standard. The problem is that every human body works differently, and a doctor needs to learn how a general human body works to make a better educated guess, however, this generalization rarely applies to the specific scenario. What if each individual was able to learn the unique specifics of how their body worked? They could make more educated/specific determinations affecting their own health (with potentially less adverse effects than the current state of western medicine). We formulate a theory based upon the known knowledge/information that we have available, into which we eventually act upon with the hope of a desired/intended outcome.

Based upon the results of the actions of the previously thought theory, we now have more information in which to base future judgments, theories, and/or decisions off of, with the ability of making a more educated guess based upon the previous experience/information. If every theory in which we base future decisions off of is backed by more [objective] information, we are exponentially capable of making better decisions. And based upon the results of said actions we learn something, or we gather information, which guides the future decisions. In other words—anytime we are trying to make changes to our body, we're merely guessing; but we try to make as educated of a guess as possible in the hope that the decision will be more effective or conducive towards our intent or goal, relative to a less educated guess. Said another way, no matter what we are guessing, we increase our chances of increasing effectiveness the more educated of a guess we can make which is going to be supported with more accurate, relative, and objective data.

As such, there is an ongoing need for an improvement upon current body fat measurement, assessment, and analysis systems ("system" including various apparatuses of various technologies with methods of use for various purposes) with increased usability, accuracy, specificity, repeatability, and data analysis performance.

SUMMARY OF THE INVENTION

Various embodiments of the invention generally relate to an improved device and method for monitoring changes in body fat and providing device which to better understand the causes of changes. In its most simplistic form, the essence/purpose of the device is to make improving health as easy as possible for anyone to do themselves; or as a tool for anyone desiring to gain insight into how various physiological stimulus (lifestyle habits) affects any aspect of someone's health. Our current societal status quo is that everything should be "as easy as taking a pill." The device's approach to accomplishing this is by figuring out how people's body's react to their lifestyle choices, to then give those people a better understanding of how their body's work, in order to empower them to make better choices in improving their health and quality of life. The device comprises of 1) a means to accurately assess, measure, monitor, and/or track changes in the body, 2) store and analyze data, and 3) provide interpretation of data.

Every body is different and reacts differently to various stimuli based on many factors, so there needs to be a way to determine the effects of various lifestyle changes. The present invention is a culmination of superior accuracy, repeatability, specificity, ease of use, data analysis, and data interpretation. The benefit of repeated accurate and specific measurements allows for better interpretation of data, and therefore more effective suggestions and solutions to the users lifestyle decision-making and behavior improvements. The essence of the invention utilizes a form of non-invasive subcutaneous sensory, to include any form of energy reflection (i.e. LED light, NIR light, ultrasound, and potentially any other technologies known in the art of non-invasive sub-cutaneous sensory, (like using a smartphone camera and LED light combination), to analyze the thickness of different tissues at specific sites (to include, but not limited to SCAT, muscle, bone, and visceral fat) with the intent to track all changes (i.e. changes to SCAT thicknesses) to provide the information necessary to make better educated decisions on how to make beneficiary/positive changes (i.e. dietary habit changes, exercise protocols) in the body based off of the users goals.

The technology of the handheld embodiment is three-fold: 1) sensor(s) to determine the thickness of the SCAT, visceral fat in the organs, and/or muscle/lean tissue at specific sites, and 2) hardware which provides communication between the device software and the user various details to include, but not limited to: instructions on taking readings, reading and analyzing results, changing profiles, real-time imaging of sensory information, recommendations on behavior changes based off of results, and 3) software to analyze and interpret data. The invention could contain all of the required hardware/components necessary to fulfill the needs of the purpose, or it could utilize components from external sources by means of direct or indirect coupling and uncoupling means.

Many variations of data interpretation and correlation are possible which include, but are not limited to: 1) tracking of specific SCAT sites trends, 2) tracking trends of overall BF, 3) comparison of site changes, 4) recommendations and education to users based off available data referenced to user goals, 5) comparison of data with other variables to include, but not limited to: body weight, sleep, energy levels, nutritional information, daily activity, exercise habits, Heart-Rate Variability (HRV), blood lab data, DNA/genetic information, mental function variables, 6) comparing data with a 'fitness goal' to assess whether or not the 'intended program/changes' taken by the user are having desired results, 7) estimating key hormone levels (to include, but not limited to, cortisol, insulin, testosterone, estrogen, thyroid related, adrenals, growth hormone, progesterone).

In one embodiment, the device comprises a standalone device that can perform its function independent of additional devices. The essence of the standalone device is to be able to take readings on a user, display the readings to the user, provide an interface between the user and software of device, and to communicate the information with external sources.

In another embodiment, the device comprises an integrated device that utilizes the resources of an external source in order to perform its function. The essence of the integrated device is to be able to do the same things as the standalone device but with utilizing (piggy-backing on) as much resources from other devices as possible, to the extent of only existing as an application on external device. An example is to have the device utilize a smart phone's resources instead of providing its own, to include but not be limited to, screen, computing resources (CPU, memory, etc), communication resources (Wi-Fi, cellular), sensory resources, and energy resources.

In still another embodiment, the device comprises a worn garment or accessory that contains sensors and other essential hardware necessary in monitoring and measuring different metrics on/in a human body real-time, and for extended periods of time. The essence of this device is to provide a means for people to get same/similar information from the body as in the first two embodiments, but to be able to have it done much more conveniently (i.e. the user doesn't have to take clothing off to take reading, the readings are done automatically, etc) and to be able to get much more data than the previous embodiments. This embodiment collects the data and communicates with external sources to include, but not be limited to, smartphones, computers, tablets, etc. Examples of accessories include, but are not limited to, watches, wristbands, headbands, necklaces, skin-coupling device, shirt, shorts, trousers, socks, or any other accessory that stays with a user for long periods of time that easily, comfortably, and effectively monitors, measures, tracks, and/or assesses any metric of bodily function which would be conducive to the essence of the device, while being as convenient for the user.

BRIEF DESCRIPTION OF THE DRAWINGS

FIG. 12-1 depicts a flow chart of a method of operating a portable subcutaneous fat diagnostic device for use in an embodiment;

FIG. 12-2 depicts a flow chart of a method of operating a portable subcutaneous fat diagnostic device for use in an embodiment;

DETAILED DESCRIPTION OF THE DRAWINGS

Figure 1:
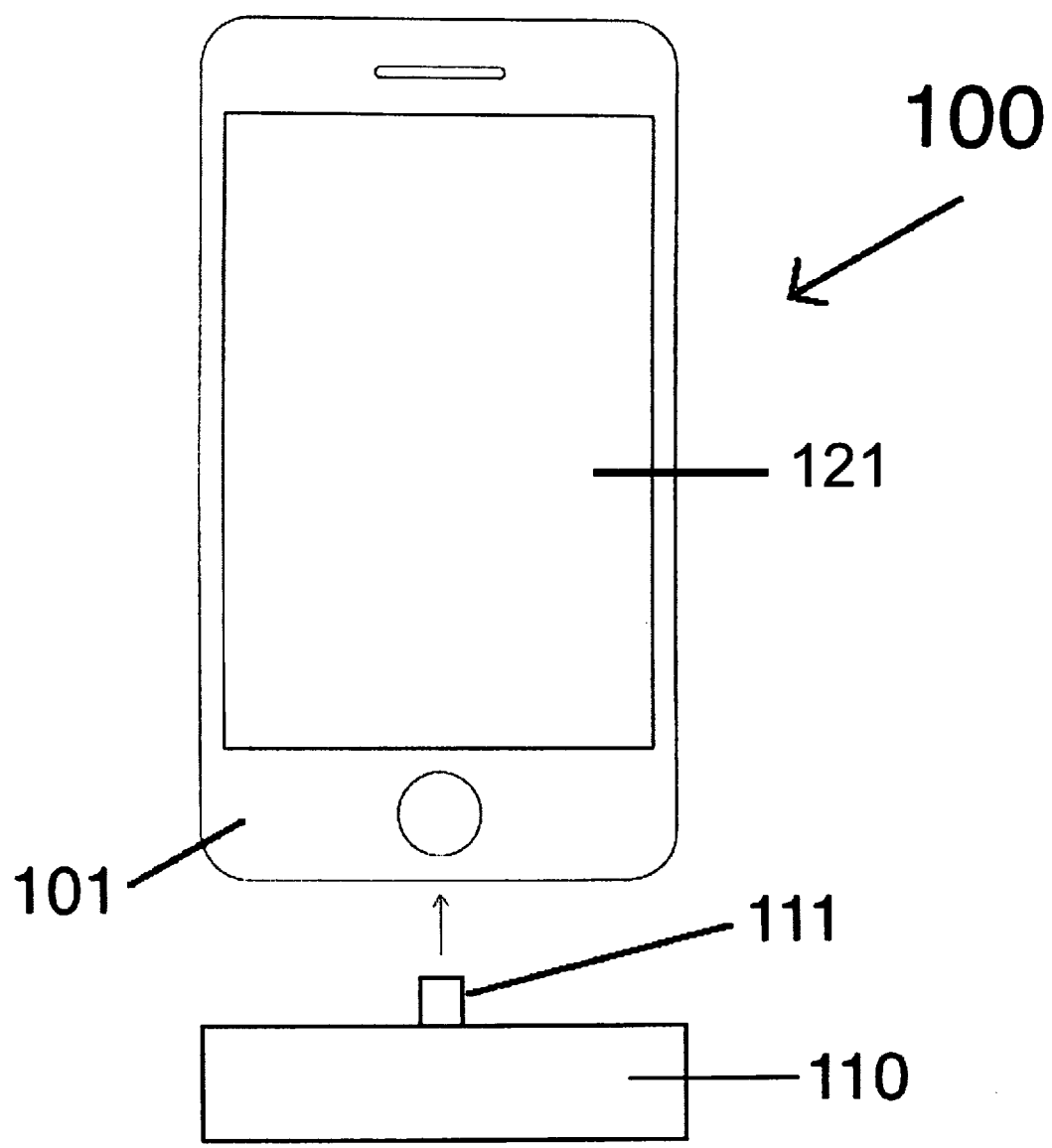
FIG. 1 depicts a portable subcutaneous fat diagnostic device in use with an external device according to an embodiment.
Figure 2:
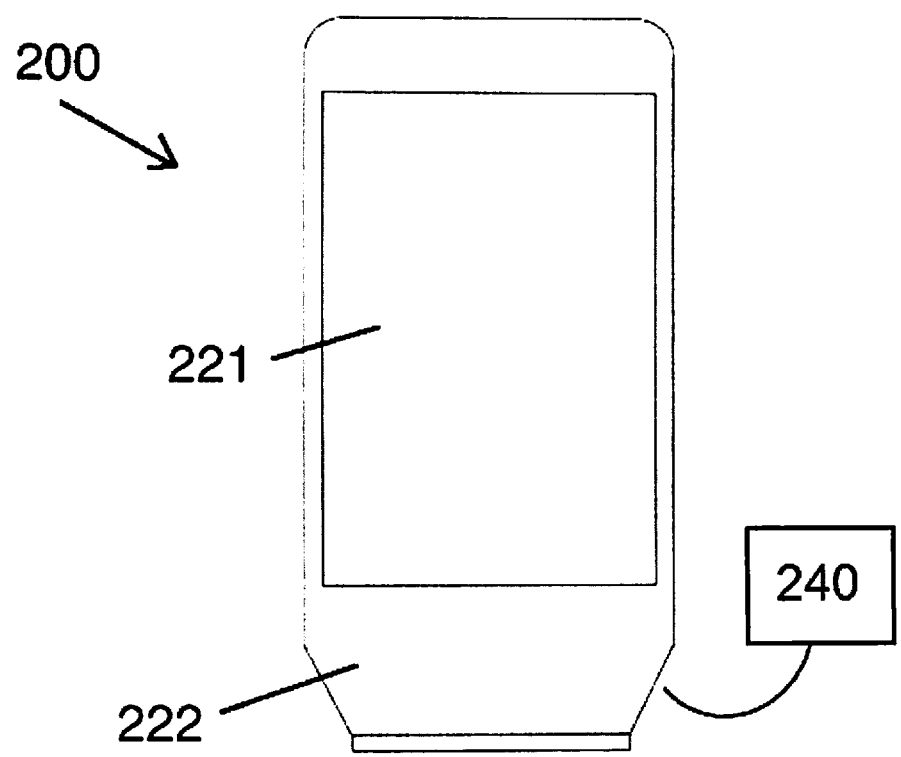
FIG. 2 depicts a portable subcutaneous fat diagnostic device according to an embodiment.
Figure 3:
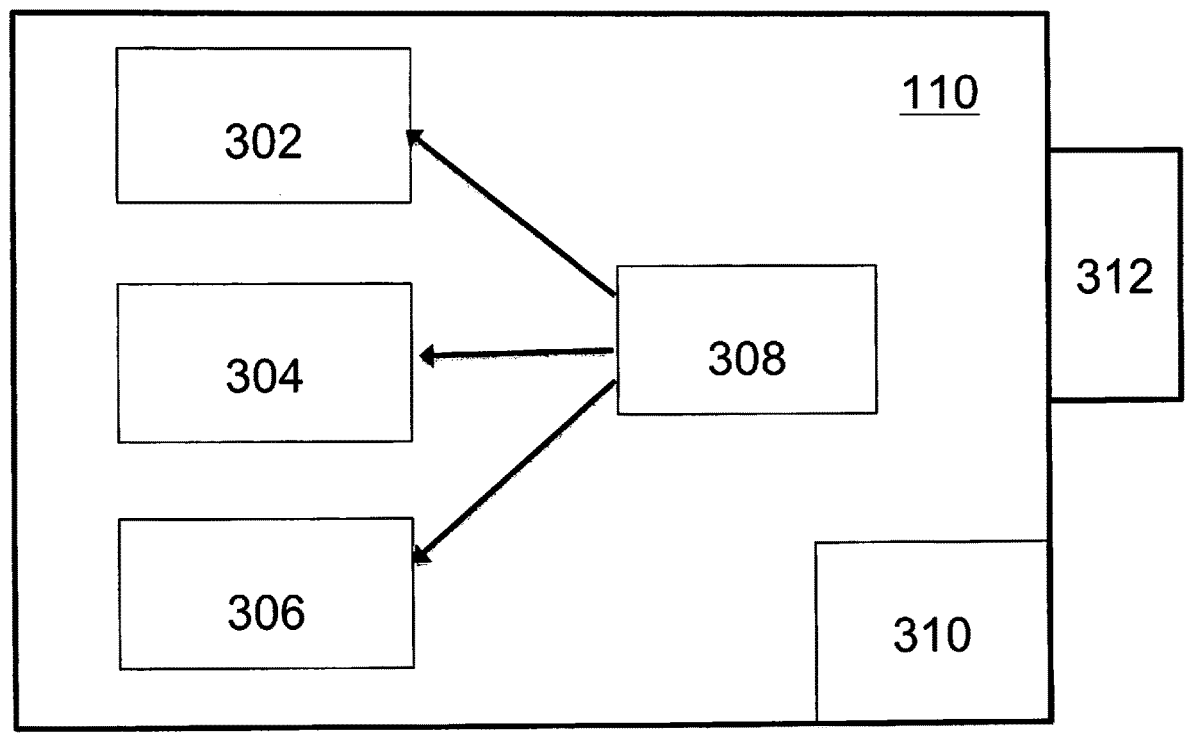
FIG. 3 depicts a block diagram of device components of a portable subcutaneous fat diagnostic device according to an embodiment.

Referring to FIGS. 1-3, a subcutaneous fat diagnostic device adapted for coupling to a mobile device is shown according to an embodiment of the invention. In embodiments, device 100 can comprise a housing 110 that is sized to accommodate various internal components of device 100. As illustrated in FIGS. 1 and 2, in various embodiments, the size and dimensions of housing 110 can vary according to design specifications and user preferences with FIGS. 1 and 2 each being exemplary embodiments. Housing 110 can be fabricated from various materials such as, but not limited to, polycarbonate, polypropylene, polyethylene, or other suitable materials that could be manufactured in any form conducive to usage of device. FIG. 3 illustrates the various components of device 100 included in housing 110. In embodiments, device 100 can comprise at least one emitter source 302, a first sensing element 304, and a second sensing element 306 each arranged within housing 110 and operatively coupled to a power source 308. Power source 308 can comprise a battery, a power supply, an AC/DC or DC/AC converter, a charged capacitor, combinations thereof, or other suitable technologies in various embodiments.

In embodiments, device 100 can comprise a communication element 310 comprising a wired (e.g., micro-USB element 111 as shown in FIG. 1), or wireless connection to communicatively couple device 100 to a mobile device 101.

For purposes of this disclosure, mobile devices may include, but are not limited to, any electronic mobile device adapted to access a wired or wireless network, such as a mobile phone, a personal digital assistant, a wireless laptop computer, a personal computer, and combinations thereof by way of non-limiting examples. Networks may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between the mobile device and other devices (e.g., remote computing systems, routers, mobile devices). Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication between the mobile device and other devices.

Additionally, housing 110 of device 100 can comprise various coupling features 312 including, but not limited to, hook-like components, coupling links with or without safety enclosures, adhesives, hook-and-loop, components using suction (using negative fluid and/or gas pressure to create a partial vacuum for purposes of adhering to an object), components using static electricity, components using magnetism, designs and components utilizing friction, cording or wiring of any material that "plugs into" external device, fasteners, and all other methods and technologies in the art of coupling and uncoupling that would be conducive to the essence of the device. Any securing, supporting, and/or coupling characteristics could change in size, shape, and/or position in ways that are conducive to the essence of the device. Supportive components could be made from any material that would be conducive to the essence of the device to include, but not be limited to, metal-like materials, wood-like materials, plastic-like materials, and any other material known in the art of manufacturing.

In embodiments, emitter source 302 can generate and emit light emissions (e.g., LED, near infrared interactance (NIR), laser, etc.), sound emissions (e.g., ultrasound, radar), electrical transmissions and/or other suitable technologies known to the art of non-invasive sensory, whether in isolation or in combinations thereof. First and second sensing elements 304, 306 can comprise ultrasonic detectors, photodiode, optical detectors, phototransistors, or other suitable sensing elements, each configured for detecting specific body characteristics. For example, second sensing element 306 can be used for the purpose of providing increased accuracy in repeatability of readings. Such sensing elements can be configured to detect parameters such as heart pulses, skeletal tissue, direction of the device relative to all dimensions in space, temperature of contact surface, or for measuring distance from bodily landmark or reference point (i.e. elbow, chin, knee, etc) to site on users body, assessing pressure of device against body. Although a single emitter source is discussed in the various embodiments herein, it should be noted, however, that device 100 can comprise fewer or more emitter sources and/or sensing elements.

As shown in FIG. 3, device 100 can further comprise a charging port 310 formed in or on housing 110 for charging power source 308 and/or for transferring information from device 100 to mobile device 101. Additionally, device 100 can comprise status illuminators (not shown) arranged on a surface of housing 110 to provide status information related to, e.g., device placement altering instructions, device angle altering instructions, sensory information quality, charging level of power source.

In embodiments, device 100 can comprise signal processing circuitry arranged within or external to housing 110. For example, in various embodiments, the diagnostic device can be implemented as either an integrated device (100), which utilizes the processing capabilities of an external device such as mobile device 101, or as a standalone device 200 (FIG. 2) comprising circuitry 240. As illustrated in FIG. 2, device 100 can comprise a display unit 221 that displays information processed by circuitry 240. Display unit 221 can comprise a liquid crystal display, LED display, OLED display, PLED display, or other suitable technologies, which can be operated utilizing various means for interaction and input between the user and device, such as, e.g., touch screen, keypad buttons, gesture monitoring or combinations thereof provided by the device or mobile device 101. In embodiments, display unit 221 can be arranged on a front surface 222 of device 200, but may vary in other embodiments such as that of FIG. 1, wherein display unit 221 comprises a user interface 121 of mobile device 101. In other embodiments, device 100 can further comprise an audio unit (not shown) comprising an audio output device such as speaker to emit sound from device 100 and/or an audio input device such as, e.g., a microphone for purposes of voice recognition, voice dictation/instruction, recording audio, or the like.

Figure 4:
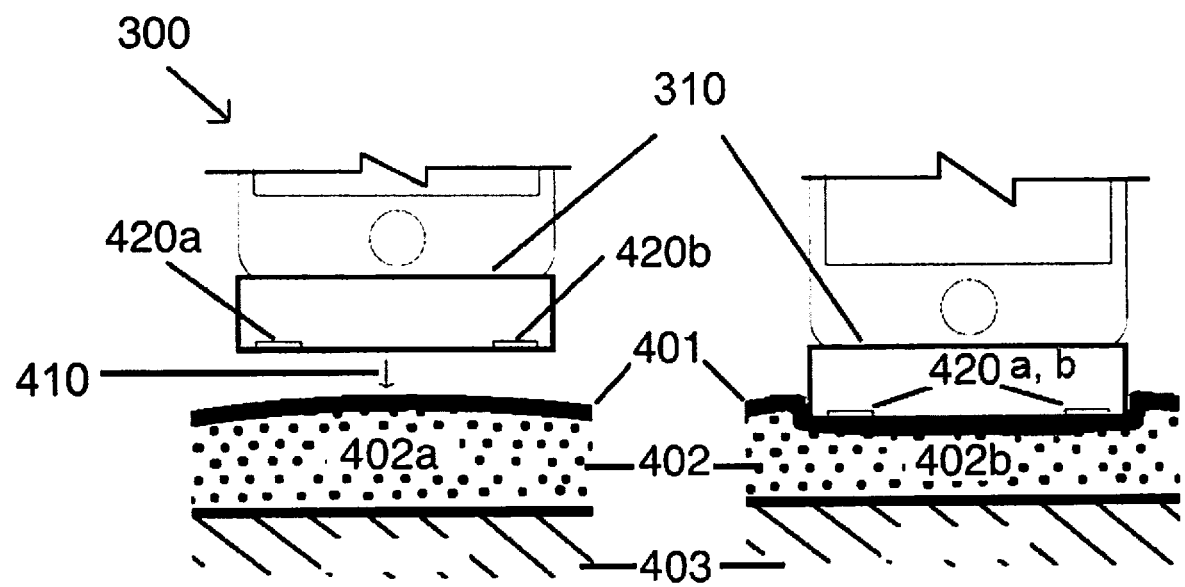
FIG. 4 depicts use of a portable subcutaneous fat diagnostic device according to an embodiment.

Referring to FIG. 4, a subcutaneous fat diagnostic device is shown according to an embodiment. In embodiments, device 300, which incorporates all the functionality of, and similar features to both devices 100 and 200, further comprises at least one pressure sensor 420a, 420b arranged in or on housing 110. Pressure sensors 420a, 420b can comprise any suitable sensing technology such as, e.g., pressure switches, pressure transducers, strain gauges, MEMS sensors, or the like. Although in FIGS. 4A and 4B two pressure sensors 420a and 420b are shown, it should be appreciated by one skilled in the art that fewer or more sensors can be provided as desired.

Figure 5A:
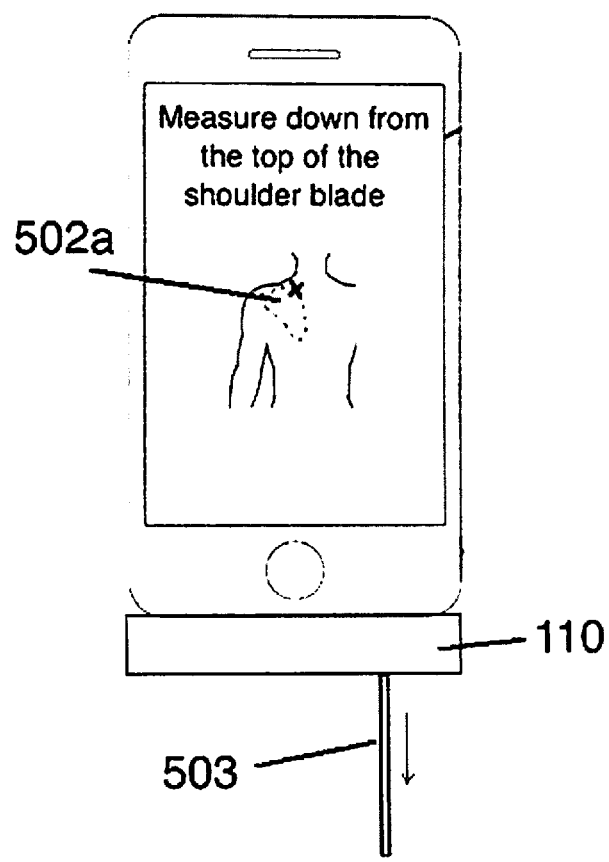
FIG. 5A depicts a portable subcutaneous fat diagnostic device in use with an external device according to an embodiment.
Figure 5B:
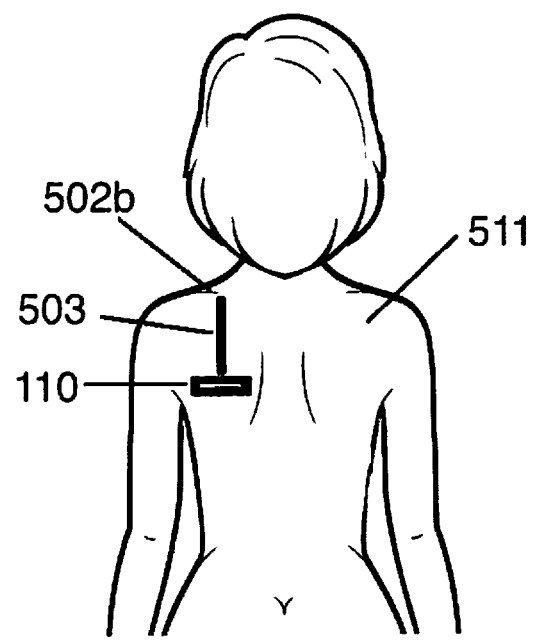
FIG. 5B depicts use of the portable subcutaneous fat diagnostic device of FIG. 5A by a user according to an embodiment.

In use, pressure sensors 420a, 420b can be used to increase the accuracy of readings by ensuring that readings are consistent and taken at the same pressure every time, which is important due to the impact that pressure has on the thickness of SCAT 401. As device 300 is placed against the skin 401 with force 410, the SCAT is deformed between the skin 401 and the underlying tissue 403 from an undisturbed thickness 402a to a compressed thickness 402b. In other embodiments, referring now to FIGS. 5A and 5B, devices 100, 200, or 300 can further comprise an attachment device 503 that extends out of the device to a predetermined distance for purposes of landmarking against a physical body 511 (refer, e.g., to FIG. 5B). For example, in FIG. 5A, the device is instructing a user as to where a landmark should be placed on the user using a visual representation 502a of a landmark. As depicted in FIG. 5B, device 100, 200, or 300 utilizes the attachment device 503 as a guide in determining the placement of the device in relation to a landmark, such as landmark 502b. Such an embodiment can be advantageous in maximizing consistency and accuracy.

Figures 6A, 6B:
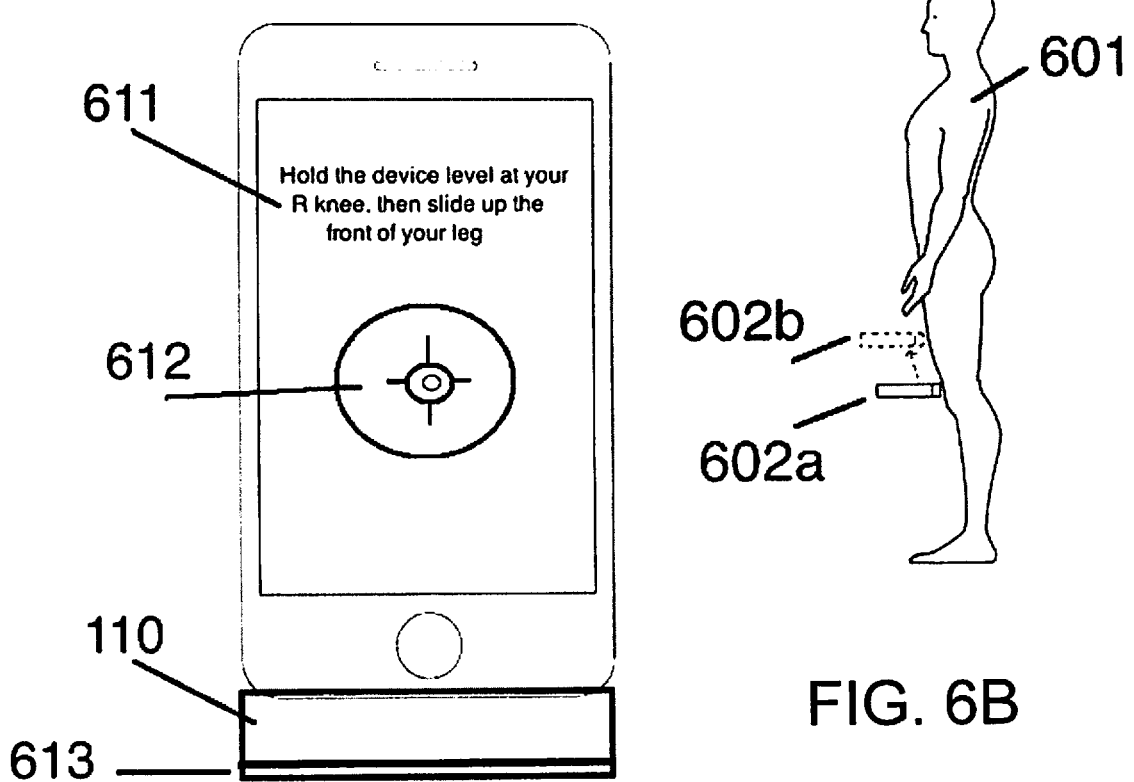
FIG. 6A depicts a portable subcutaneous fat diagnostic device in use with an external device according to an embodiment.
FIG. 6B depicts use of the portable subcutaneous fat diagnostic device of FIG. 6A by a user according to an embodiment.

In still other embodiments, devices 100, 200, or 300 can further comprise a motion-sensing element 613 (refer, e.g., to FIGS. 6A and 6B) arranged in or on housing 110 to determine movement along a user 601 to measure distance from the landmark 602a to the reading location 602b. In combination with motion-sensing element 613, the device utilizes spatial sensors (represented by imagery 612) to determine the distance traveled between a landmark and a reading location, which is then communicated to a user via a display such as display unit 611.

Figure 7:
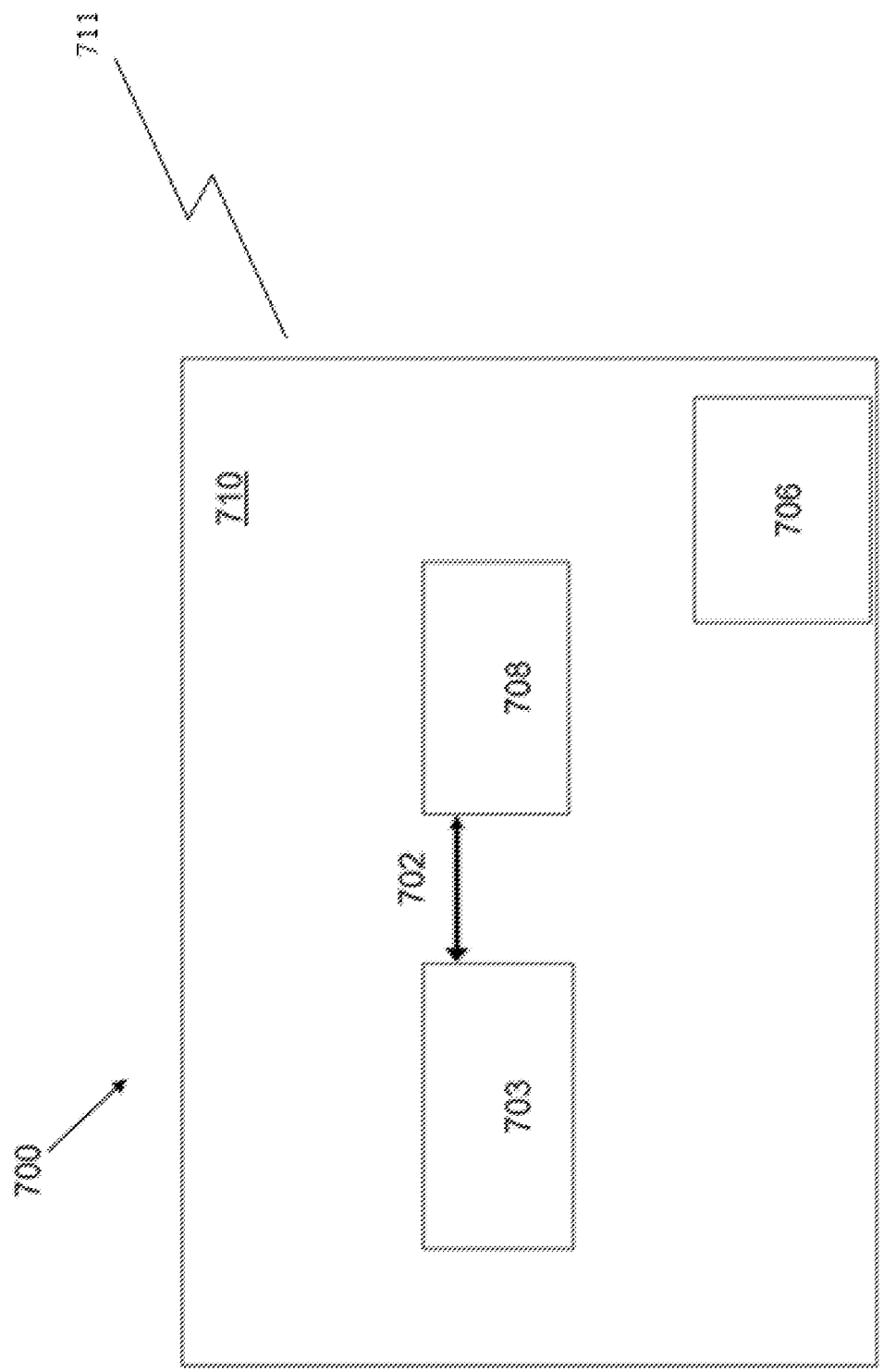
FIG. 7 depicts a block diagram of a portable subcutaneous fat diagnostic device according to an embodiment.

Referring now to FIG. 7, a subcutaneous fat diagnostic device is shown according to an embodiment. In embodiments, device 700 can comprise a worn garment 710 or accessory that contains sensors and other essential hardware necessary in monitoring and measuring different metrics on/in a human body real-time, and for extended periods of time. Worn garment 710 can include, but is not limited to, watches, wristbands, headbands, necklaces, skin-coupling device, shirt, shorts, trousers, socks, or any other accessory that stays with a user for long periods of time that easily, comfortably, and effectively monitors, measures, tracks, and/or assesses any metric of bodily function which would be conducive to the essence of the device, while being as convenient for the user. The essence of this device is to provide a means for people to get same/similar information from the body as in the first two embodiments, but to be able to have it done much more conveniently (i.e. the user doesn't have to take clothing off to take reading, the readings are done automatically, etc) and to be able to get much more data than the previous embodiments.

This embodiment collects the data and communicates with external sources 711 to include, but not be limited to, smartphones, computers, tablets, etc.

In embodiments, device 700 can comprise wiring 702 arranged in or on garment 710 to connect components such as components 704, 706 of device 700, which can include, but not be limited to energy sources, energy generating components, sensory components, communication components, or anything else conducive to the essence of the device. For example, sensory components could include, but are not limited to, subcutaneous adipose tissue sensors, internal or external body temperature, skin perspiration, movement within three-dimensional space, pressure of sensors against body or pressure of body against external sources (i.e. detecting changes of low back SCAT due to sitting back in chair), skeletal muscle, blood glucose levels, hormonal levels, etc. Technology of assessing internal bodily metrics can include any known technology present or future in the art of internal bodily metrics [self-quantification]. Once the data is gathered from the sensory components, device 700 can comprise a display 721 such as unit 221 discussed with reference to FIG. 2 to either transfer or display information on the garment or transferred.

As discussed above, components 704, 706 can include energy storing or producing components. Much of the hardware/components of the garment will require energy/electricity to function, so the garment will include means to store or produce energy/electricity to power components. In embodiments, such components can include fabrics that generate electricity using technologies and processes such as, e.g., thermoelectric, electromagnetic, solar, kinetic energy harassing, and all other technologies in the art of electricity generation and textiles. In other embodiments, device 700 can also include energy storage components instead of or along with energy producing components, which are used to power any components of device requiring such.

Figure 8A:
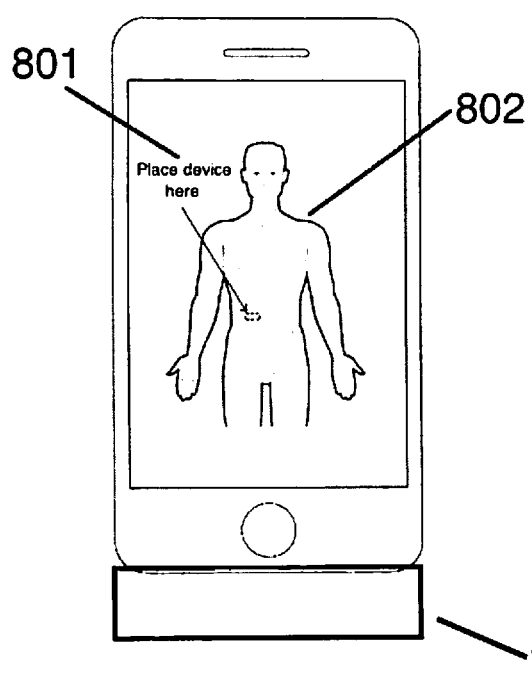
FIG. 8A depicts an exemplary graphical user interface of a portable subcutaneous fat diagnostic device in use with an external device according to an embodiment.
Figure 8B:
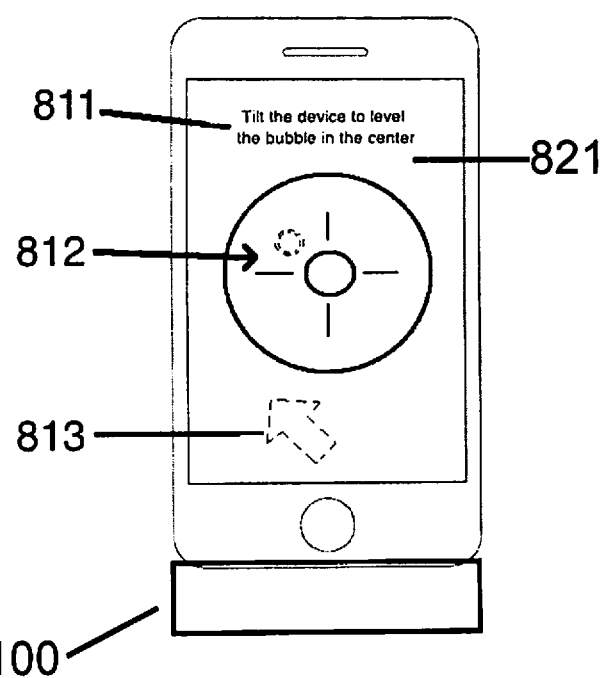
FIG. 8B depicts an exemplary graphical user interface of a portable subcutaneous fat diagnostic device in use with an external device according to an embodiment.
Figure 9:
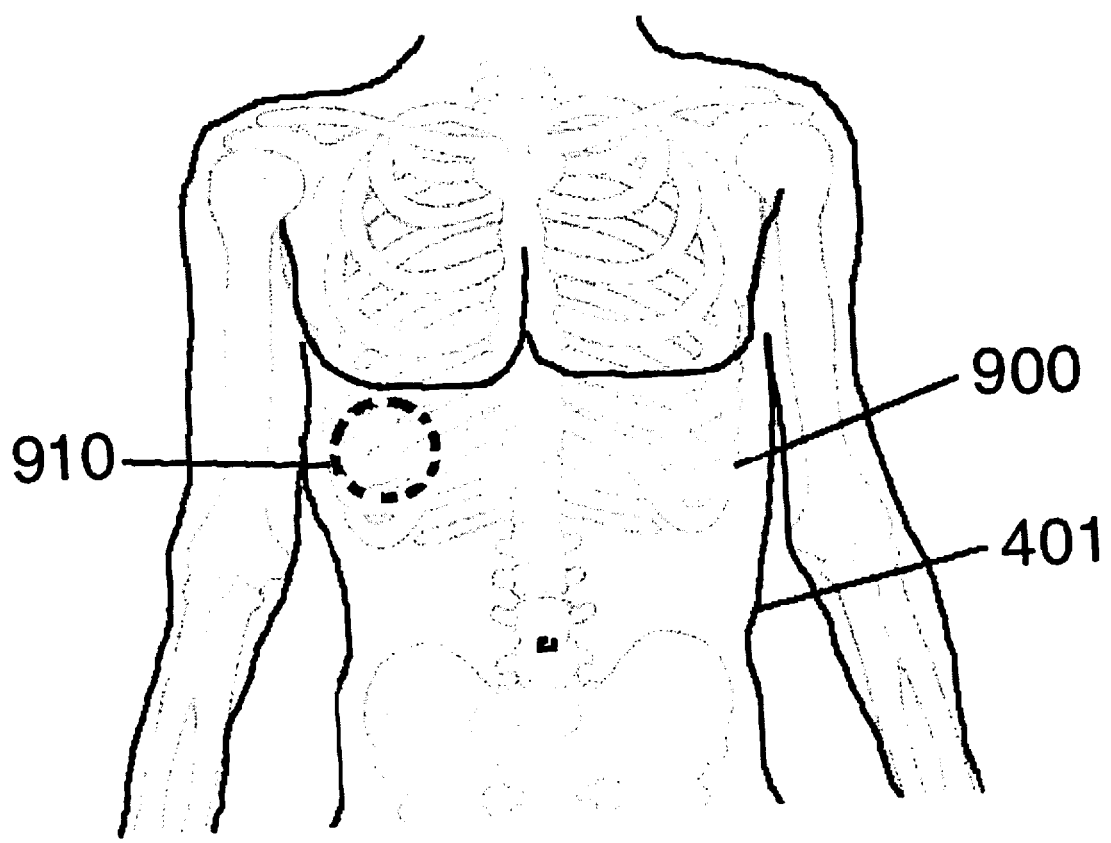
FIG. 9 depicts internal landmarking of a user's body for use by a portable subcutaneous fat diagnostic device according to an embodiment.
Figure 10A:
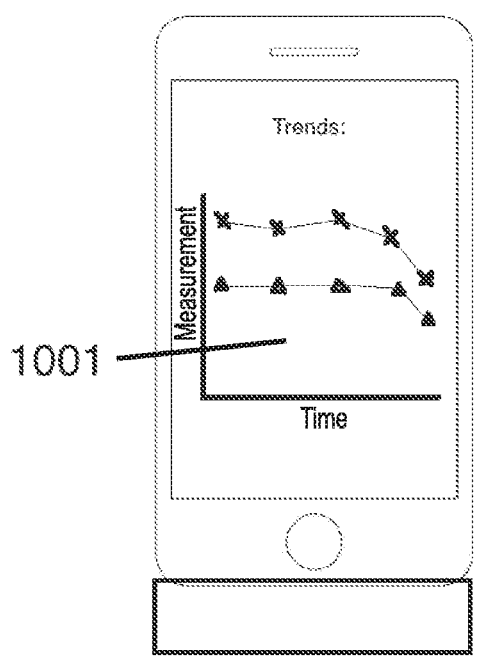
FIG. 10A depicts an exemplary graphical user interface of a portable subcutaneous fat diagnostic device in use with an external device according to an embodiment.
Figure 10B:
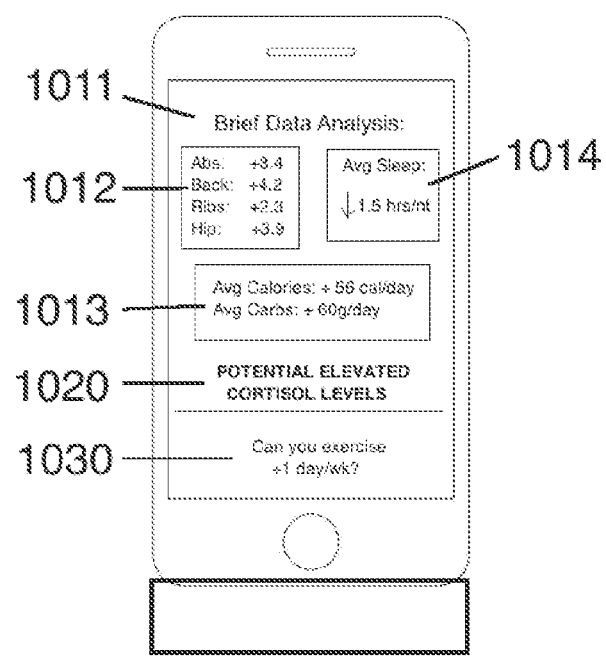
FIG. 10B depicts an exemplary graphical user interface of a portable subcutaneous fat diagnostic device in use with an external device according to an embodiment.

Referring to FIGS. 8A-8B, an exemplary graphical user interface is shown according to an embodiment. For example, in FIGS. 8A and 8B, device 100 as discussed with reference to FIG. 1 is instructing a user via a display unit 821 on where to place device 100 on a physical body using written instruction 801 and visual instruction 802. FIG. 8B represents an embodiment of device 100 using real-time information to determine instructions 811 to a user. In this specific embodiment, device 100 is using spatial awareness 812 and displaying the real-time information to the user, whereby 813 represents the use of arrows to instruct the user on which way to tilt the device. With reference to FIG. 9, an exemplary embodiment of device 300 using internal landmarks within the body is shown. By taking measurements at a site and also detecting the skeletal structure 900 under the skin 401 (refer, e.g., to FIG. 4), the device can use the landmarks to instruct the user to take all repeated readings in the exact same spot to increase consistency and accuracy of information. The device can essentially take an initial "snapshot" of the skeletal device below 910 during the initial reading which to compare to all future readings. In other embodiments, referring now to FIGS. 10A and 10B, the device can also display past readings to a user via display unit 1001. In FIG. 10B, the device displays the summary of readings 1011 to the user. 1012 embodies where the current reading is relative to previous reading(s). 1013 embodies additional relevant data, in this case nutritional, relative to previous points in time. 1014 embodies additional relevant data, in this case sleep amounts, relative to previous points in time. 1020 is an embodiment of displaying calculated analysis of all data available relative to the user, in this case concluding that the user's hormone levels may be out of balance based off of data. 1030 embodies a suggestion provided by the device based off of the data analysis.

Figure 11:
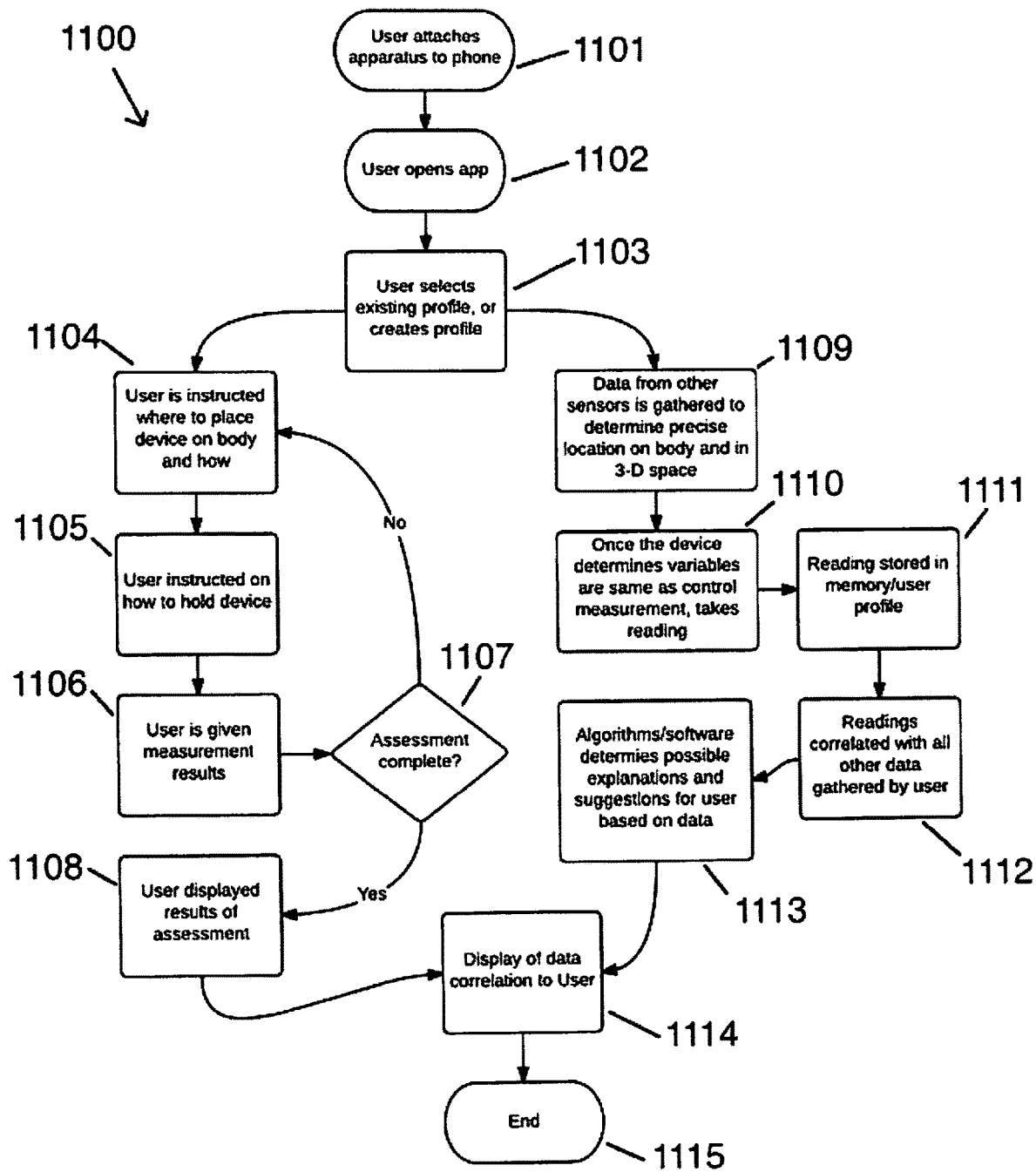
FIG. 11 depicts a flow chart of a method of operating a portable subcutaneous fat diagnostic device for use in an embodiment.
Figures 1, 12:
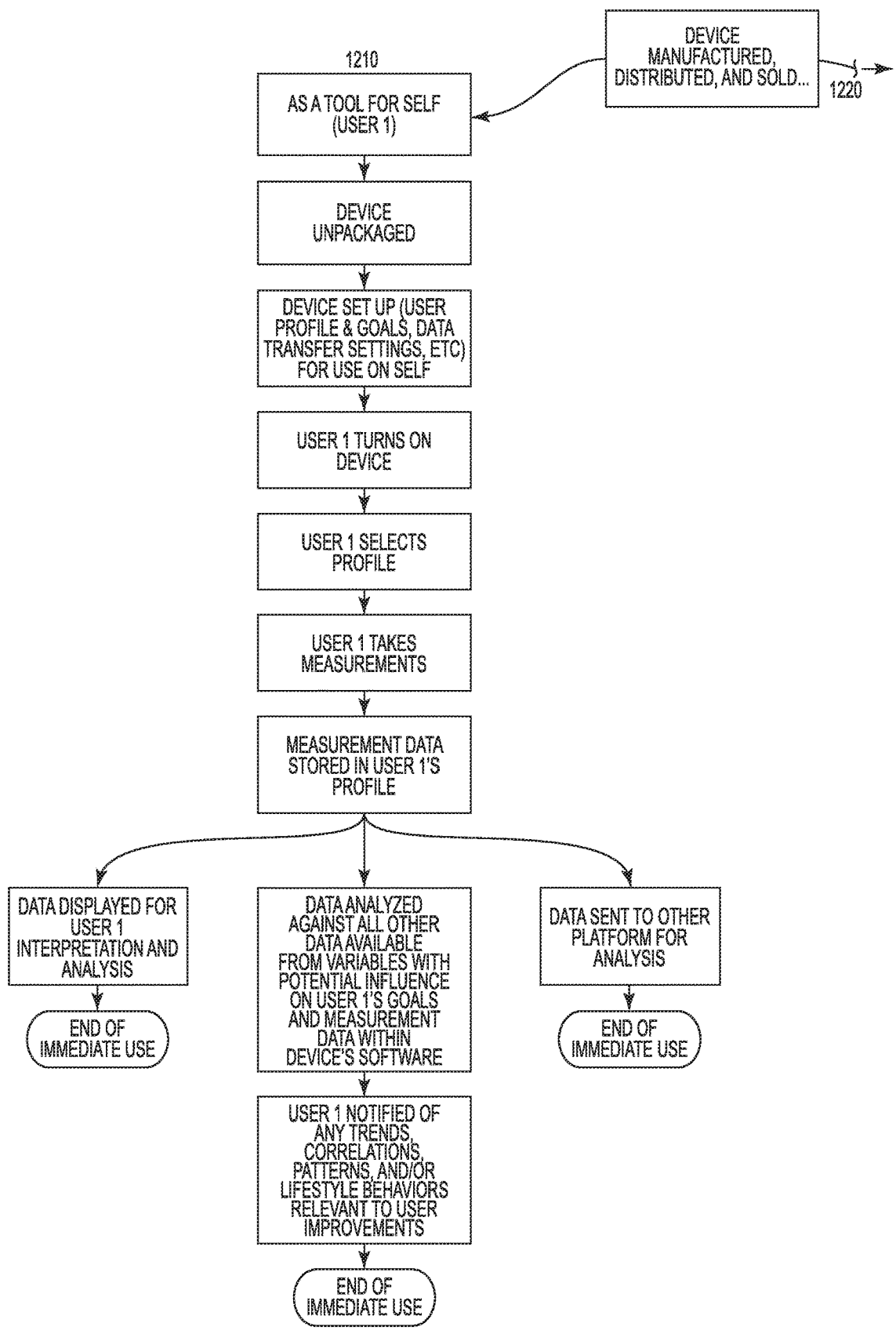
FIG. 12 depicts a block diagram representation of FIGS. 12-1 and 12-2.
Figures 2, 12:
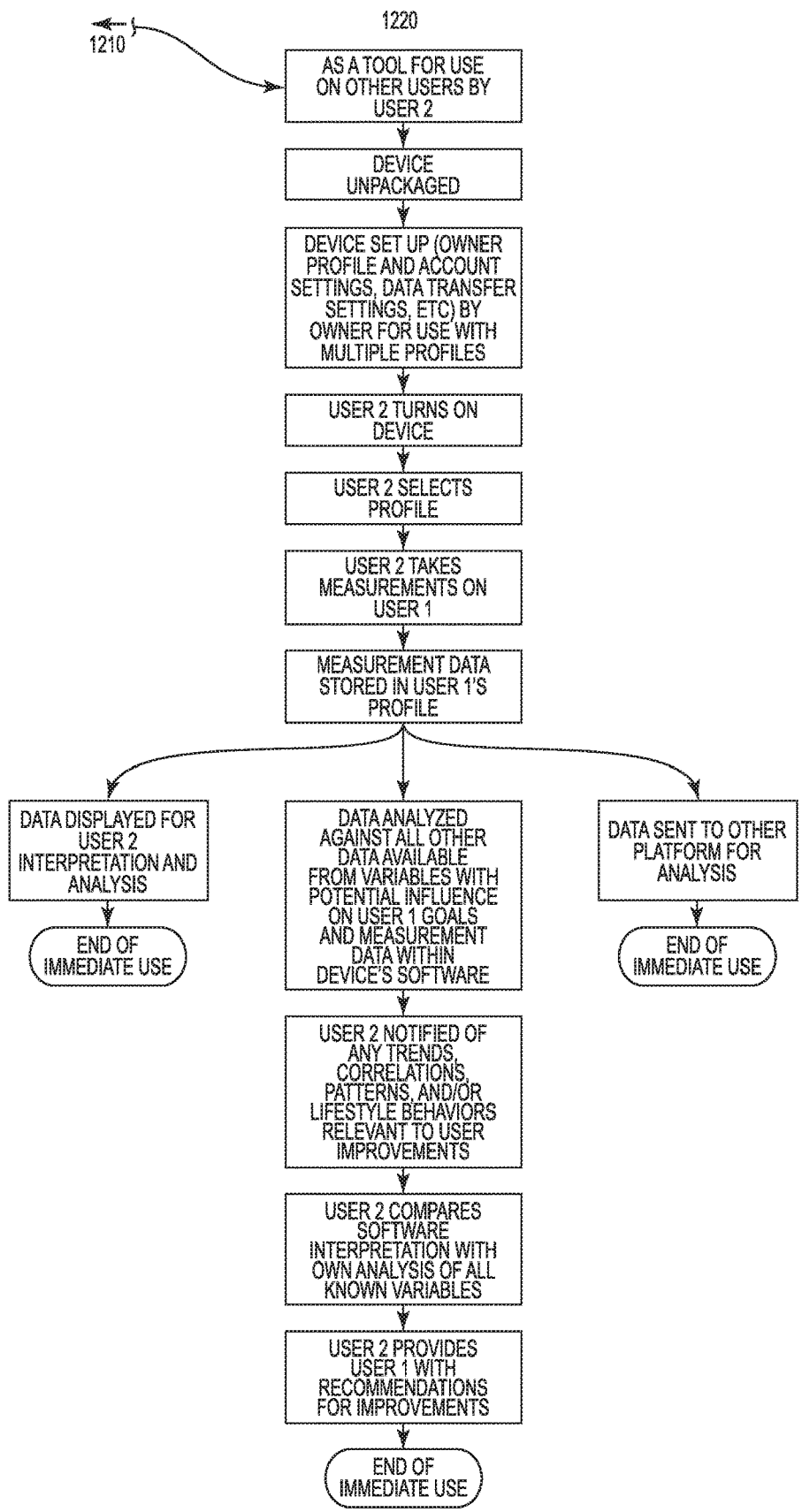

Referring now to FIG. 11, a flow chart of a method 1100 is shown. In operation, the various embodiments of the diagnostic device 100 discussed herein can be used by an individual on themselves (User 1), or by someone else (e.g., a personal trainer or a health and wellness consultant) using the device on another (User 2), as illustrated in further detail in FIGS. 12-1 and 12-2. At 1101, a user attaches the device to a mobile device such as mobile device 101 and opens a software application at 1102. The software application is then displayed on a user interface such as display unit 121 or 221. At 1103, a user (e.g., user 1 or user 2) selects a profile stored on either device 200 or mobile device 101, and is then instructed through the assessment process at 1104. For example, when a user sets up their profile, they will take initial measurements at any and all selected sites on the body for a "baseline reading" in which to compare all other readings off of in reference to specific location on the body to improve accuracy of comparative data. Metrics and methods used to ensure that different, related, or future readings are as relatable as possible (maximizing control of measurement by limiting variables that could skew data) include, but are not limited to, using metrics such as pressure of device against user, positioning and angle of device and sensors relative to three-dimensional space, positioning and angle of device and sensors relative to reference-able structures and features of the body, both internally and externally.

At 1105, the user is first instructed as to how the device should be properly oriented. As the user places the device on or near instructed site, the device assists the user by giving directions/corrections on where to accurately take the reading (refer, e.g., to FIG. 8B). Next, at 1106, the user is provided with measurement results, which are displayed on a display unit, e.g., units 121, 221, at 1108 following the verification of a completed assessment at 1107. Instructional methods include, but are not limited to, visual (i.e. pictures, videos, text, lights), auditory (i.e. sounds, verbal instructions), somesthetic (i.e. vibrations, movement), such that the instructions do not have to be limited to pre-programmed commands from the device, as the device can also utilize real-time imaging and comparison to instruct the user. The purpose of the device instructions to the user include, but are not limited to, proper placement of the device on the users body, tips on taking measurements, proper pressure of device on user, proper angle of device on user, proper levelness of device in three-dimensional space, notifications, and changing testing sites.

As measurements are being taken, data from other sensing elements (e.g., 306, 420*a* and 420*b*) is simultaneously gathered at 1109 to determine the precise location on a body and in 3-D space. At 1110, once the device determines the variables are the same, readings are taken and the data is stored at 1111 (to include, but not be limited to the device, on a server, in the cloud) and can then be sent via WiFi, bluetooth, USB, and other methods of communication known in the art, to other platforms to include, but not limited to, other online profiles, other software, other hardware or devices. Wherever the data resides, it is up to the user/software/platform to determine how the data is interpreted, for example, whether the data will be stored on the device itself or an external device. Once every site has been assessed/measured (depending on a user's preferences and goals/intended results), the readings can be correlated with other corresponding data and sent to other sources in addition to being stored on the device at 1112.

Figure 14:
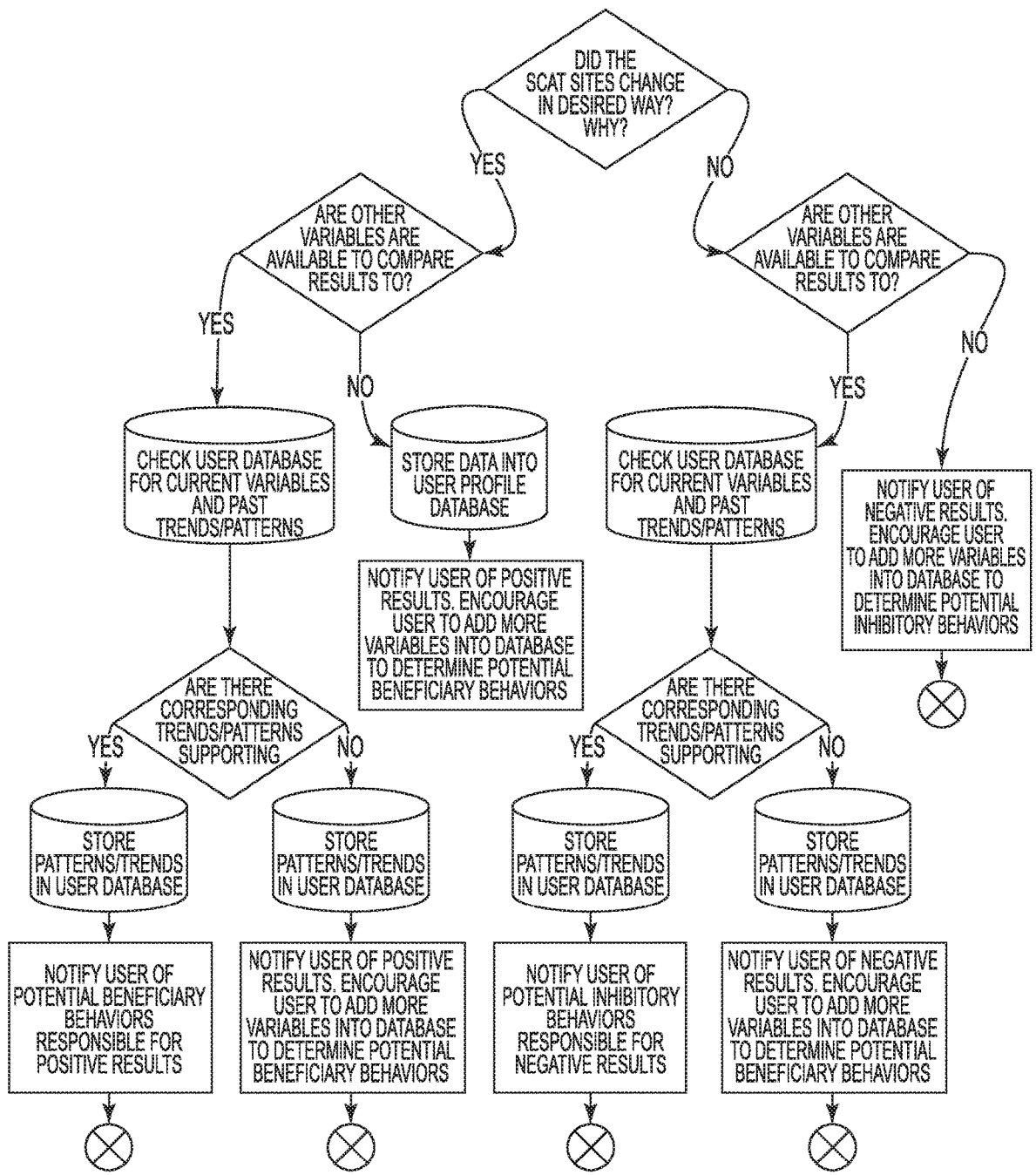
FIG. 14 depicts a basic algorithm/decision making flowchart of the operation of a portable subcutaneous fat diagnostic while the device is in use.

At 1113, the data is assessed using various algorithms (refer, e.g., to FIG. 14) implemented on the processors of either the device itself or mobile device 101 to determine possible explanations and suggestions for the user. When creating the algorithms used in the invention to correlate data, it will consist of permutations of variables. The number of variable combinations utilized by the software algorithms include, but not be limiting in the scope of the invention, are: basic metrics (age, gender, body weight, nationality, geographical location), overall body fat percentage, visceral fat variables, sleep variables, energy level variables, nutritional variables, daily activity variables (to include time and type of activity), exercise habits, Heart-Rate Variability (HRV), Heart Rate [over time], blood lab data, DNA/genetic information, blood type, mental function variables, health goals, SCAT site variations, SCAT sites relativity to one another, speculated or known hormone levels, and medications.

The number of different permutations created and utilized by the software can be determined using the following equation. $N!/(n-r)!(r!)$; with n being the number of possible variables and r being the number of variables utilized. To list examples of all of the combinations of variables the software could potentially use, we will use the following equation, $N!/(n-r)!(r!)$, and the following letters to represent the different variables:

a—age
b—gender
c—body weight
d—nationality
e—geographical location
f—body fat variables (overall percentage, overall amount, type of fat)
g—medical history (types, frequencies, and duration of diseases and/or ailments)
h—sleep variables
i—energy level variables
j—nutritional variables
k—daily activity variables (to include time and type of activity)
l—exercise habits
m—Heart-Rate over time+Heart Rate Variability (HRV)
n—hydration levels
o—blood lab data p—DNA/genetic information
q—blood type
r—mental function variables
s—health goals
t—SCAT site variations, locations, changes
u—SCAT sites relativity to one another
v—speculated or known hormone levels
w—medications Given the 23 variables above, the following combinations can be made given the combination/permutation formula for a total of 8,388,607 combinations of variables the software will be analyzing, if limited to only the listed variables.

| number of variables used | number of possible combinations |
|---|---|
| r = 1 | 23 |
| r = 2 | 253 |
| r = 3 | 1771 |
| r = 4 | 8855 |
| r = 5 | 33649 |
| r = 6 | 100947 |
| r = 7 | 245157 |
| r = 8 | 490314 |
| r = 9 | 817190 |
| r = 10 | 1144066 |
| r = 11 | 1352078 |
| r = 12 | 1352078 |
| r = 13 | 1144066 |
| r = 14 | 817190 |
| r = 15 | 490314 |
| r = 16 | 245157 |
| r = 17 | 100947 |
| r = 18 | 33649 |
| r = 19 | 8855 |
| r = 20 | 1771 |
| r = 21 | 253 |
| r = 22 | 23 |
| r = 23 | 1 |
| total combinations | 8388607 |

Whatever the user is able to enter into the device, the device will assist the user in making sense of it all by being able to present the information in any way to the user to come to their own conclusions; or to assist the user by making suggestions to possible correlations, outcomes, patterns, etc that are of relevancy towards the users purpose.

The software will anonymously gather all of the data of its users to learn the impact of different variables on specific body types and situations. For example, the software would notice over time if 80% of the Caucasian female users between the ages of 31-34 living in the Midwest with an O+ blood type and take SSRI anti-depressant medications with similar eating and exercise patterns all have a unique sensitivity towards a specific type and amount of glucose in the evening which causes restless sleep—which would be noted and potentially used later as a suggestion towards a user with similar variables in the future. Essentially, the software will take all of the information and learn how all of the variables impact people to be able to give better and better suggestions to users in the future as the software learns and evolves. Ultimately, if the users submit their information along with a DNA sample, the software could determine how particular variables impact different genetic variables relative to one another, and potentially what parts within human genetic sequences are responsible for particular traits as they relate to health.

The software would also notice symptoms that correlate to certain disorders and whether or to what degree they would affect other devices, and what those symptoms would be. For example, the software understands and notices the correlations and affectedness between the Adrenal, Ovarian/sexual, and thyroid devices.

Once the data has been transferred to the user's profile, then at 1114 it can be viewed on external sources (to include, but not limited to, Apps, websites, computer software) for any purpose (to include, but not limited to, basic analysis, comparing with other variables being tracked by other software or devices, monitoring long and short-term changes and trends). At any time, a user can look at any data and corresponding trends collected on a profile (completed any time before or after assessment) a user defines measuring preferences, goals/intended results within profile which determines what sites will be assessed. Following completion of an assessment, the user may then close and exit the app at 1115.

An example of usage with the worn garment device 700, would be a user wearing said garment throughout the day as it is tracking certain metrics. Options could include, but not be limited to, heart rate, heart rate variability, skin temperature, means to measure body fat at specific sites related to worn garment, and skin perspiration.

Figure 13:
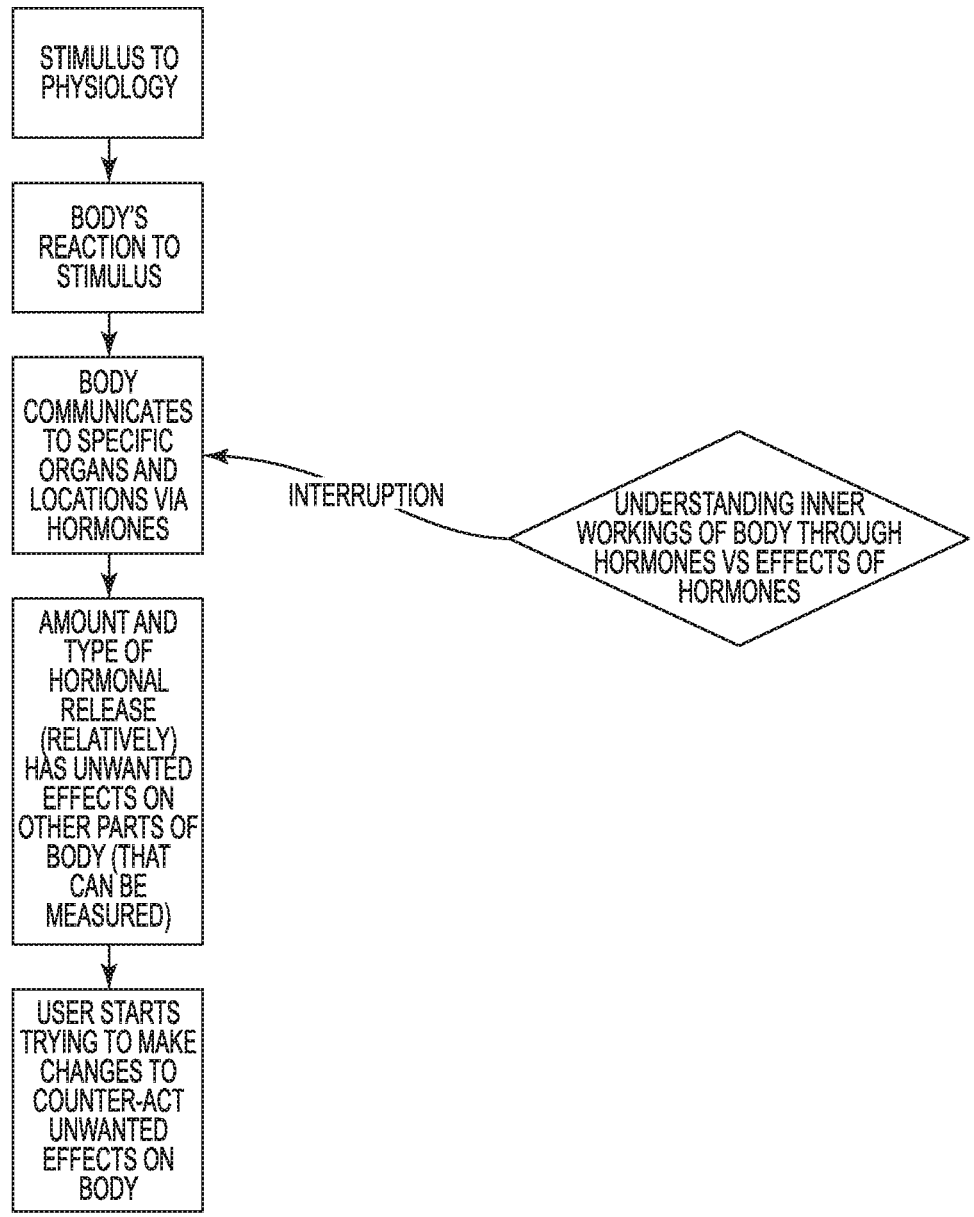
FIG. 13 depicts a basic representation of a body's hormonal reactivity to stimuli.

In this particular example, the user wants to improve their diet, and they want to know how their body responds to their current dietary habits. As the user is wearing the garment, they signify to the software, whether it be through a smartphone app or on the garment itself, when the user begins eating. This input triggers the garment to monitor changes in metrics, say skin temperature, perspiration, and body fat storage in three different areas to see what affects the meal had on the users body. This information can be used for a multitude of reasons, to include, but not be limited to, determining if the user has some sort of allergic response to the food, if the food caused the user to store fat in certain areas in the body following the meal, or as a means to detect symptoms of hormonal reactions (refer, e.g., to FIG. 13) to the food.

In another example, the garment device 700 can be worn while the user is exercising to determine what kind of fuel source the user's body is burning (glucose and fat), how much calories are expended, determining the amount of site specific body fat reduction post-exercise, as well as crossing this information in addition to nutritional information.

In any and all circumstances of usage with device 100, the accumulated data gathered about a person's body allows for an increased understanding of how said body works by allowing the cross-referencing of different variable data (i.e. lifestyle behaviors and habits) that has either a positive or negative effect for use of analysis by a living person or programmed software.

EXAMPLE 1

Fat Loss/"SCAT Assessing"

"Joe" wants to lose fat specifically around his abs to feel confident taking his shirt off in the summer. Joe goes on the "Diet X" hoping to accomplish this goal, and at the beginning of the diet he takes different readings for his SCAT baseline measurement: Site A is next to belly button, Site B is at top of hip bone, and Site C is between the two at the anterior-superior iliac spine (ASIS), Site D at the chest, and Site E on the back of the arm. Sites A-C are where he especially wants to lose the SCAT; as well as tracking his nutritional information from Diet X. Joe takes readings at these 5 sites every other day for 3 weeks to track the change trends.

"Diet X" can be used interchangeably with any other behavior/lifestyle change, to include but not limited to exercise variables, sleep habits, supplementation, hydration, etc. In any and all examples, the device software is learning how different variables affect the user's body, becoming smarter, or learning, in its ability to give guidance to the user.

Ex 1.1: At the end of the 3 weeks, Joe sees all of the sites trend decreases, especially in the desired sites around his abdominal area. Joe has confirmed that Diet X works for his intents and purposes, so he continues the diet.

Ex 1.2: At the end of the 3 weeks, Joe doesn't see any significant changes to any of the sites, especially is his desired sites, even though his body weight has steadily decreased. According to the calculated body fat percentage from the analyzer, his percentage has increased slightly confirming that he is in fact losing lean/muscle mass. Joe discontinues Diet X to try something new.

Ex 1.3: At the end of the 3 weeks, Joe sees Sites C and D decrease significantly, but not significant changes to A-C. Joe discovers that Diet X has a "SCAT loss effect" on his body, but not specifically where he wants to decrease SCAT, so he may wish to discontinue Diet X for a different diet.

Ex 1.4: At the end of the 3 weeks, Joe doesn't see any significant changes to any of the SCAT sites, but his body weight has increased. Diet X doesn't have the desired effects.

Ex 1.4.1: Joe's overall body fat has stayed the same, meaning that the combination of Diet X with his exercise routine seems to be increasing lean mass.

Ex 1.4.1a: Cross-referencing the above data with nutritional data that he has been tracking for 10 weeks, Joe correlates his lean mass increases with an increase in protein/fat/overall calorie and decreased carbohydrate intake diary changes Ex 1.4.2: Cross-referencing the data from above with BIA data, Joe's intracellular/extracellular water levels have increased. This limited data may suggest that he has elevated inflammation levels in the body. More data would be needed to conclude hypothesis, but Joe now has the awareness that inflammation may be negatively affecting his health and fitness goals.

EXAMPLE 2

Muscle/Lean Tissue

Joe wants build more muscle in his chest and arms. Before beginning "Workout X" program, he takes baseline measurements of his muscle/lean mass at various sites on the chest and arms. Over the next 6 weeks, Joe has takes measurements around his body to track lean tissue mass to determine the effectiveness of Workout X on his body and lifestyle. If the results are not what Joe's looking for, he may wish to modify his exercise and/or nutrition habits based off of his own interpretation and understanding or off of the guidance of the device software.

EXAMPLE 3

Optimizing Overall Health

Joe wants to improve his health—he feels sluggish, is mentally foggy, doesn't sleep well, is overweight, and basically has all of the signs of metabolic syndrome. To improve his health, he wants an easy, inexpensive and non-invasive way to better understand what is going on in his body in order to make beneficial changes to his body via lifestyle/habit changes.

Using the analyzer for 6 weeks, in addition to other devices tracking lifestyle variables, the analyzer notices that Joe's body stores fat at particular sites indicative of [to include but not limited to] non optimal levels of key hormones that influence fat storage: cortisol, insulin, testosterone, estrogen, thyroid related, adrenals. The analyzer explains what his storage pattern potentially means in regards to his health and fitness goals, and gives him suggestions on what to potentially try next to make positive changes. Once Joe decides which change he wants to make, he annotates that within the analyzer, so after another 6 weeks the analyzer learns what effect the change had, and is then able to make better suggestions for Joe based off of the changes in his body from his lifestyle/habit changes.

EXAMPLE 4

Bio-Hacking

Joe is an avid health enthusiast that is always experimenting with different ways to optimize his health. In order to accurately understand the effects of his bodily experiments, he needs as much information on the effects as possible. Joe will not only be able to track the changes in body fat at any storage site, but will also gain an understanding of the experiment's effects on his hormones based off of the changes in body fat storage sites provided by the device software. The more information that Joe has on the changes in his body as a result from his experiment, the more knowledge is gained on the effects of particular habits/variables on his body.

EXAMPLE 5

Fitness Professional Tool

Joe is a professional assisting people with their health and fitness goals. Joe wants a tool to easily, and accurately assess changes in people's bodies that he is advising. If Joe has a tool that accurately determines what the effects of his recommended changes are, he is better educated on how the person's body reacts to various stimuli, giving him the ability to make better recommendations to a person he is working with to achieve their goals.

EXAMPLE 6

Worn Garment to Determine Effectiveness of Weight-loss Efforts/Strategies 6.1: Joe wants to know which workout routine burns the most fat in his stomach area. Joe wears the garment and tracks energy expenditure during Workout A, as well as post-exercise site-specific fat utilization for one week. The following week Joe does the same thing with Workout B, and then compares the results of the two workouts to determine which one is more conducive/effective towards his exercise goals.

6.2: Joe wants to know which diet burns the most fat in his stomach area. Joe wears the garment and tracks energy expenditure and site-specific body fat storage for three weeks while on Diet A. Joe then tries Diet B for three weeks, and then compares the results of the two diets to determine which one is more conducive/effective towards his health goals.

6.3: Joe wants to determine if he has food allergies that he is unaware of that may be affecting his weight loss goals. He wears the garment day-to-day and logs the time and ingredients of his meals. The garment monitors changes in Joe's body following the meal to look for signs of food allergies or sensitivities. After being used long enough, the software is able to determine what ingredients are causing the unwanted reactions and notifies Joe of suggested nutritional options to try to see if they alleviate the unwanted reactions after meals.

EXAMPLE 7

Correlations of Symptoms in Relation to [Potential] Hormonal Imbalances 7.1: The user tracks that their energy levels drop in the afternoon, consumes a high amount of salty food during the day and sugary foods at night, is getting limited quality and/or quantity of sleep, and relatively/proportionately high fat storage in the mid-section, the software alerts the user that all of these symptoms are indicative of Adrenal fatigue
7.2.1: Knowing the information from 7.1, the software 1) can alert the user that they are more susceptible to other disorders now, so look out for the following symptoms estrogen dominance, or start tracking metrics related to estrogen dominance
7.2.2: Software notices that the user has a high extracellular fluid ratio, has been declining in activity levels, has been increasing overall body fat amounts, and has been consuming a high percentage of their carbohydrates as sugars—then alerts the user that these are all symptoms of estrogen dominance (and they may want to consult a physician; or contact a nutritionist; or suggest particular supplements or dietary changes, etc)
7.3: In addition to everything in 7.1 and 7.2, the user has been tracking a consistently low body temperature, which is indicative of hypothyroidism, which the device notifies the user that all of these symptoms are related, and provides suggestions on what they can do or how to look deeper (i.e. suggest a new metric to begin tracking that is related to suspected condition), or what other symptoms to be aware of.

Various embodiments of devices and methods have been described herein. These embodiments are given only by way of example and are not intended to limit the scope of the invention. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the invention.

Persons of ordinary skill in the relevant arts will recognize that the invention may comprise fewer features than illustrated in any individual embodiment described above. The embodiments described herein are not meant to be an exhaustive presentation of the ways in which the various features of the invention may be formed or combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

The invention claimed is:
1. A non-invasive monitoring system comprising:
   a garment configured to be worn on a user's body to measure internal metrics of the body;
   an arrangement of a plurality of sensors on the garment, the arrangement such that the plurality of sensors corresponds to an orientation of the garment in three-dimension space and a reading location of the garment on the user's body according to a landmark and a distance traveled between the landmark and the reading location, wherein each of the sensors includes:
      an emitter configured to generate and direct at least one source of electrical current through the user's body from a first fixed point corresponding to one of the plurality of sensors to a second fixed point corresponding to a second one of the plurality of sensors when the garment is worn; and
      a sensing element configured to detect the directed at least one source of electrical current,
      wherein a signal corresponding to the thickness of both visceral fat and subcutaneous fat is generated at each of the reading locations based upon a sensed component of the at least one source of energy; and
   a remote processing device configured to track and display changes in the metrics over an extended time.
2. The non-invasive monitoring system of claim 1, wherein each of the plurality of sensing elements is selected from the group consisting of:
   an ultrasonic sensor;
   an optical sensor;
   a kinetic sensor;
   an electrical impedance sensor; and
   a bioimpedance sensor.
3. The non-invasive monitoring system of claim 1, wherein the plurality of sensors are communicatively coupled to a remote processing device.
4. The non-invasive monitoring system of claim 1, wherein the plurality of sensors are configured to determine a location of fat storage, and determine a quantity of fat storage at the location.
5. The non-invasive monitoring system of claim 3, wherein the remote processing device is configured to track bioimpedance to determine a blood glucose level.
6. The non-invasive monitoring system of claim 1, wherein the plurality of sensors are communicatively coupled to the remote processing device via a communication element comprising wired, wireless, or other techniques known in the field of data transfer.

7. The non-invasive monitoring system of claim 1, wherein the system is configured to send data corresponding to the sensed component of the at least one source of energy to a data storage device.

8. The non-invasive monitoring system of claim 1 further comprising a power source configured to power the emitters and the sensing elements.

9. The non-invasive monitoring system of claim 1 further comprising an audio unit configured to transmit and receive audio signals.

10. The non-invasive monitoring system of claim 1 further comprising a pressure sensor.

11. The non-invasive monitoring system of claim 1 further comprising:
a display unit arranged on the garment;
a processing unit configured to convert the signals generated by the sensing elements into data signals for display on the display unit; and
a data transfer unit for transferring the data signals to the remote processing unit.

12. A non-invasive method of using a garment to measure a metric:
providing the garment configured to be worn on a user's body, the garment comprising a plurality of sensors in an arrangement, wherein each of the plurality of sensors includes:
an emitter configured to generate and direct at least one source of energy through the user's body when the garment is worn; and
a sensing element configured to detect the directed at least one source of energy and generate a signal corresponding to the metric;
activating the emitter to direct the at least one source of energy through the user's body;
sensing, with the sensing element, a portion of the directed at least one energy source that has travelled through the user's body;
generating a signal corresponding to the data sensed by at the sensing element of at least one of the plurality of sensors;
analyzing the signal to generate a site-specific indication of a location of both visceral fat and subcutaneous fat; and
displaying the analyzed signal on a display unit,
wherein the plurality of sensors determines an orientation of the garment in three-dimensional space and a reading location of the garment on the user's body according to a landmark and a distance traveled between the landmark and the reading location.

13. The method of claim 12, further comprising determining a quantity and a location of fat at a storage site.

14. The method of claim 13, further comprising tracking a quantity of the fat tissue.

15. The method of claim 12, further comprising sensing a blood glucose level.

16. The method of claim 15, further comprising determining an insulin level from the sensed blood glucose level.

17. The method of claim 12, further comprising:
sensing, with a second sensing element, a plurality of physiological parameters associated with the metric;
generating a first and second signal corresponding to the measured data sensed by the first and second sensing elements;
analyzing the sensed data from the first sensing elements and the second sensing elements; and
displaying the analyzed data on the display unit.

18. The method of claim 12, and further comprising tracking changes in a quantity of fat at a location.

* * * * *